United States Patent [19]

Bernstein

[11] 4,305,720
[45] * Dec. 15, 1981

[54] GENTAMICIN ASSAY AND PRODUCTS THEREFOR

[75] Inventor: David Bernstein, Sykesville, Md.

[73] Assignee: Becton Dickinson & Company, Paramus, N.J.

[*] Notice: The portion of the term of this patent subsequent to Dec. 16, 1997, has been disclaimed.

[21] Appl. No.: 68,165

[22] Filed: Aug. 20, 1979

[51] Int. Cl.³ ............................................. G01N 33/54
[52] U.S. Cl. ................................. 23/230 B; 23/915; 422/55; 422/61; 424/12
[58] Field of Search ............... 424/12; 23/230 B, 915; 422/55, 61

[56] References Cited

U.S. PATENT DOCUMENTS

| | | | |
|---|---|---|---|
| 3,074,853 | 1/1963 | Brewer | 424/12 |
| 3,639,558 | 2/1972 | Csizmas et al. | 424/12 |
| 3,951,748 | 4/1976 | Devlin | 23/230 B X |
| 4,069,352 | 1/1978 | Parsons, Jr. | 23/230 B X |
| 4,100,268 | 7/1968 | Scherr | 424/12 |

Primary Examiner—Arnold Turk
Attorney, Agent, or Firm—Louis E. Marn; Elliot M. Olstein

[57] ABSTRACT

A gentamicin protein conjugate adsorbed on a solid support, in particular, polystyrene particles, is crosslinked by a crosslinking agent to increase the stability of the supported conjugate. The particles also generally include an adsorbed protein to increase the strength of the crosslinking network. An improved conjugate is provided by the use of orosomucoid as the protein. The sensitized particles can be employed in an agglutination inhibition card test.

35 Claims, 1 Drawing Figure

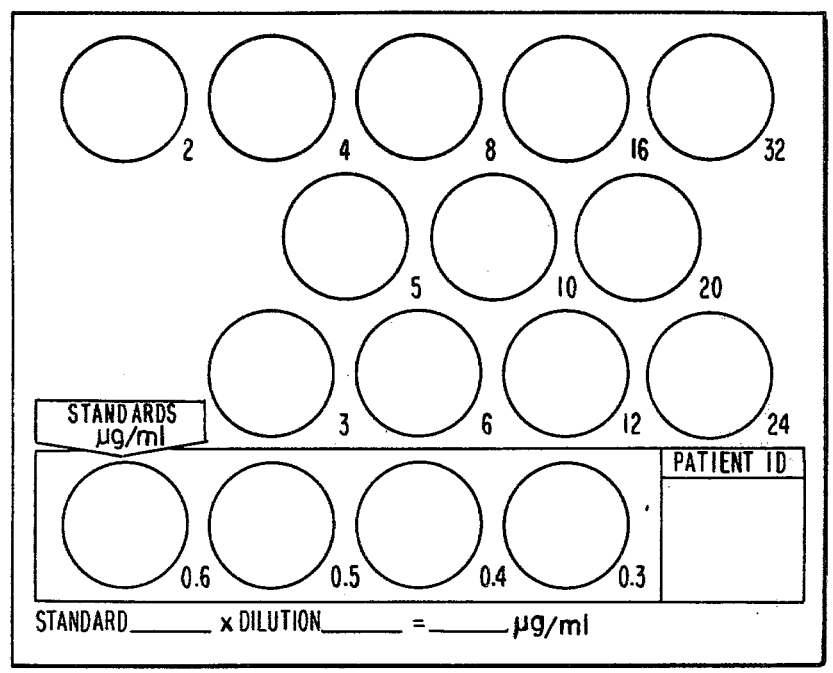

GENTAMICIN ASSAY AND PRODUCTS THEREFOR

This invention relates to an assay for gentamicin and products employed in such assay, as well as processes for producing such products.

Gentamicin, a broad spectrum aminoglycoside antibiotic, is bactericidal against many aerobic organisms, particularly Pseudomonas, Proteus, Klebsiella, *E. coli*, and Staphylococci. It is widely used in the treatment of severe gram negative bacillary infections and septicemia of undetermined etiology, alone or in combination with other antibiotics.

The desired therapeutic concentration of gentamicin is generally 4 to 8$\mu$ g/ml. Sustained peak concentrations greater than 12$\mu$ g/ml and trough concentrations greater than 2$\mu$ g/ml are potentially ototoxic and nephrotoxic, while concentrations below 4$\mu$ g/ml may not be bactericidal for some pathogens. The incidence of gentamicin toxicity in patients has been reported to be as high as 11%. Gentamicin is excreted entirely by the kidneys and in the presence of renal impairment, drug accumulation may occur. Toxicity is frequently reversible if the dosage is adjusted promptly.

Ideal pharmacologic management should involve adjustment of the individual dosage to keep the drug concentration within the narrow therapeutic range. The measurement of serum drug concentrations would be helpful for such adjustments. Several different procedures for determining gentamicin concentrations are commercially available including bioassay, radioimmunoassay, and radioenzymatic assay. The latter two require either expensive gamma or liquid scintillation counting equipment, which are not uniformly available. Bioassay is less expensive, but requires considerable technical time, prolonged incubation, and is adversely affected by many other antimicrobial agents. Therefore, many hospitals do not perform gentamicin determinations, and the selection of a safe and effective gentamicin dose remains a problem for the clinician.

U.S. Pat. No. 4,100,268 discloses gentamicin sensitized particles which are employed in an agglutination assay for gentamicin. As disclosed in the patent, gentamicin is covalently linked to a protein; in particular, bovine serum albumin, and such conjugate is then covalently coupled or adsorbed onto solid particles for use in an agglutination assay for gentamicin.

In accordance with the present invention, there is provided an improved product for use in an assay for gentamicin, and an improved assay for gentamicin.

In accordance with one aspect of the present invention, there is provided a gentamicin-protein conjugate adsorbed on a solid support, with the conjugate being crosslinked by a crosslinking agent to increase the stability thereof. Applicant has found that adsorption of a gentamicin-protein conjugate on a solid support does not have the requisite storage stability, and in accordance with one aspect of the present invention, such stability is increased by crosslinking of the conjugate on the solid support.

In accordance with another aspect of the present invention, there is provided an improved gentamicin-protein conjugate which can be supported on a solid support, either by adsorption or by covalent coupling, with such conjugate including orosomucoid as the protein.

In accordance with another aspect of the present invention, there is provided an improved assay for gentamicin, and in particular an assay which employs an agglutination inhibition test card.

In accordance with the one aspect of the present invention, gentamicin is covalently coupled to a suitable protein, followed by adsorption of the resulting conjugate onto a solid support. Such supported conjugate is then crosslinked by a suitable crosslinking agent to thereby increase the storage stability of the supported conjugate. In many cases, the concentration of the conjugate on the solid support is limited, whereby effective crosslinking of such conjugate is difficult (reduced concentration increases the spacing between the conjugate molecules). In such cases, and in accordance with a preferred aspect of the present invention, subsequent to adsorbing the conjugate onto the solid support, and prior to the crosslinking, the portions of the support free of conjugate are coated with a suitable protein, followed by crosslinking to provide a crosslinked network including the conjugate and the additionally coated protein to thereby provide for increased storage stability. Thus, in effect, the crosslinking agent forms crosslinks between the conjugate and the additional protein coated onto the solid support.

The gentamicin may be initially coupled to any one of a wide variety of proteins which do not adversely affect the gentamicin, and which would not adversely affect the subsequent assay. The protein basically functions as a carrier particle to enable sensitization of a solid support with the gentamicin. As representative examples of suitable carrier proteins for producing the gentamicin-protein conjugate, there may be mentioned bovine serum albumin, orosomucoid, ovalbumin, alpha, beta, and gamma globulins, thyroglobulin, etc. The selection of a suitable protein for use in producing the conjugate is deemed to be within the scope of those skilled in the art from the teachings herein. As hereinafter noted in more detail, the preferred protein is orosomucoid.

The gentamicin may be coupled to the protein by anyone of a wide variety of coupling agents which do not adversely affect the immuno reactivity of the gentamicin. As known in the art, such coupling is accomplished with a coupling agent having two or more reactive groups. As representative examples of such coupling agents, there may be mentioned; dialdehydes; e.g. glutaraldehyde, succinaldehyde, malonaldehyde, etc., unsaturated aldehyde; e.g., acrolein, methacrolein, crotonaldehyde, etc.; carbodiimides such as 1-ethyl-3-(3-dimethylaminopropyl) carbodiimide hydrochloride; diisocyanates; dimethyladipimate; cyanuric chloride; and the like. The selection of a suitable coupling agent for producing the gentamicin-protein conjugate is deemed to be within the scope of those skilled in the art from the teachings herein.

Such conjugate is then coated onto a solid support, i.e., by adsorption. The solid support may be any one of a wide variety of solid supports which do not interfere with the assay, and on which the conjugate can be effectively adsorbed. In the case where the supported conjugate is to be employed in an agglutination type of assay, such solid support is in the form of particles. It is to be understood, however, that the conjugate could be adsorbed on solid supports in a form other than particles wherein the conjugate is to be employed in an assay which does not require solid particles. As representative examples of suitable supports, there may be mentioned; synthetic polymer supports, such as, polystyrene, polypropylene, polyacrylates, polyamides, etc.; charcoal; lecithin/cholesterol particles and the like. The preferred support is a polystyrene, in particulate form, sometimes referred to as a polystyrene latex. It is to be understood, however, that other supports may be employed within the spirit and scope of the present invention.

Subsequent to the adsorption, the support, including adsorbed conjugate, is preferably further coated with a protein in order to provide a protein coating on the portion of the support which does not include conjugate. As hereinabove noted, such protein coating is for the purpose of "filling in the spaces" between the adsorbed conjugate so as to enable formation of an effective crosslinking network to increase stability. The protein coating may be any one of a wide variety of proteins which do not adversely affect the gentamicin and its immuno-reactivity. As known in the art, such protein coating preferably should not have immunological reactivity with any sera to be used in an assay. The protein may be one of the proteins hereinabove noted as being suitable for conjugation to gentamicin. A preferred protein coating is ovalbumin. In some cases, if the concentration of conjugate on the solid support is sufficient, coating with protein may be eliminated in that such concentration permits formation of an effective crosslink network.

The conjugate adsorbed on the solid support (which may also include further protein coated thereon) is then crosslinked by the use of a suitable crosslinking agent. Such crosslinking agent may be one of the coupling agents hereinabove described with respect to conjugation of the gentamicin to a protein to provide a gentamicin conjugate. Such crosslinking is conducted with an agent and in a manner which does not adversely affect the immuno reactivity of the gentamicin conjugate. A preferred crosslinking agent is a dialdehyde, and in particular, glutaraldehyde.

In accordance with another aspect of the present invention, gentamicin is coupled to the protein orosomucoid to provide a gentamicin-protein conjugate. Such conjugation may be accomplished by the use of a coupling agent, as hereinabove described.

The conjugate of gentamicin and orosomucoid may then be supported on a solid support, either by adsorption or by covalent coupling. Thus, for example, such conjugate may be supported by covalent bonding through one of the hereinabove noted coupling agents, by procedures known in the art, to a suitable solid support having reactive groups. Alternatively, as hereinabove described, such conjugate may be adsorbed on a solid support, such as a polymer support. The supporting of such conjugates is well known in the art, and is described, for example, in U.S. Pat. No. 4,100,268. As a result no further details are required for a complete understanding of the invention.

Applicant has found that orosomucoid is particularly suitable as a carrier protein for gentamicin in that such protein is weakly immunogenic and is capable of effectively coupling and supporting gentamicin. In addition, by employing orosomucoid as the carrier protein for the gentamicin, it is possible to produce antibodies with bovine serum albumin as the immunogenic carrier. The use of different carrier proteins, one for production of antibodies and the other in the assay, eliminates the need for cross adsorption of antisera.

The invention will be further described with respect to the following examples; however, the scope of the invention is not to be limited thereby:

EXAMPLE 1

Preparation of Rabbit anti gentamicin antisera

Gentamicin covalently coupled to bovine serum albumin (BSA) by use of 1-ethyl 3-(dimethyl aminopropyl) carbo-diimide hydrochloride (ECDI) (0.9 mole gentamicin per mole BSA) is diluted in 0.05 M phosphate buffer solution, pH 7.2, to a final protein concentration of 2.0 mg/ml and emulsified with an equal volume of complete Freund's adjuvant. One milliliter of the emulsion was injected intramuscularly into the rear flank of each of ten New Zealand albino rabbits. Rabbits were injected Day 1, 15 and boosted once per month and test bled from the medial ear artery. Antisera was diluted and reacted with gentamicin latex antigen suspension. When a satisfactory antibody titer was attained, rabbits were bled weekly. The antisera were sterile filtered, sodium azide was added to a final concentration of 0.1% and then stored at 4° C.

EXAMPLE 2

Preparation of Gentamicin Orosomucoid Conjugate

Orosomucoid was purified from Bovine serum fraction VI glycoprotein (ICN) utilizing carboxymethyl cellulose column. The first eluted peak in 0.025 M acetate buffer pH 4.0 was diluted to a final protein concentration of 6 mg/ml $E_{1\%}^{280}=8.9$ in acetate buffer. In a typical experiment 16.0 mg of orosomucoid was mixed with 300 mg of gentamicin. 750 mg of ECDI was added in 2.5 ml of acetate buffer pH 4.0. The reaction mixture was incubated for 18 hours at 4° C. and then extensively dialyzed against distilled water.

EXAMPLE 3

Preparation of Gentamicin Orosomucoid Sensitized Particles

Polystyrene latex (0.945μ 10%, Dow Diagnostics) was washed three times with 10 volumes of 0.02 M glycine buffer pH 8.6. The latex was adjusted to a final concentration of 1% latex. Gentamicin orosomucoid conjugate was diluted in distilled water to a final concentration having an optical density at 280 nm of 0.110. 5.0 ml of 1% washed latex was added to each of 5 corex glass tubes. The gentamicin orosomucoid conjugate was added in 0.100 ml increments from 0.300 ml to 0.700 ml to each tube containing latex. The tubes were vortexed and incubated for one hour at 37° C. 1.0 ml of 0.2% ovalbumin. 0.02 M glycine buffer pH 8.6 was added to each tube and the tubes were incubated for an additional 15 minutes at 37° C. The tubes were centrifuged at 2000 g, supernatant decanted and the particles resuspended in 4.0 ml of 0.02 M glycine buffer pH 8.6. 1.0 ml of 2.5% glutaraldehyde was added to each tube in order to crosslink the adsorbed protein for stability. The tubes were incubated for one hour at 37° C. The tubes were each centrifuged and washed two times with 10.0 ml of 0.02 M glycine buffer pH 8.6. The latex pellets were each resuspended in 5.0 ml of resuspending buffer containing 0.05% polysorbate 80, 0.5% ovalbumin, 0.1 M glycine buffer pH 8.6, 0.17 NaCl, and 0.1% sodium azide. The latex conjugates were then heated for two hours at 56° C., cooled to room temperature, and then assayed.

In accordance with a further aspect of the present invention, there is provided an improved assay for gentamicin, and a kit suitable for performing such assay.

In brief, there is provided an agglutination inhibition test which can be employed to measure the concentration of serum gentamicin. In particular, gentamicin sensitized particles react with anti-gentamicin antisera. The addition of a serum sample containing gentamicin inhibits the agglutination reaction. A serum sample is serially diluted, and each diluted sample is reacted with a fixed quantity of antisera and a fixed quantity of gentamicin sensitized particles. Such diluted samples are examined in order to determine the lowest sample concentration at which agglutination is inhibited. Standards, containing known concentrations of gentamicin, are reacted with the fixed quantity of antisera and the fixed quantity of gentamicin sensitized particles to determine the lowest standard concentration at which agglutination is inhibited. In this manner, the quantity of gentamicin in the sample can be determined by multiplying the reciprocal of the highest dilution of the sample showing inhibition by the concentration of gentamicin in the standard having the lowest concentration at which inhibition occurs.

In accordance with this aspect of the present invention, there is provided a kit for assaying gentamicin by an agglutination procedure which includes anti-gentamicin antisera (antibody to gentamicin) and gentamicin supported on a solid support, as hereinabove described, with the solid support being in particulate form. In accordance with a particularly preferred embodiment, the solid support is in the form of polymer particles, with such polymer particles preferably being polystyrene. In accordance with a particularly preferred aspect, the gentamicin is conjugated to orosomucoid. In accordance with the most particularly preferred embodiment, such supported gentamicin conjugate is stabilized by crosslinking as hereinabove described.

In accordance with another aspect of the present invention, there is provided an inhibition of agglutination test for gentamicin which uses a card for conducting the assay. In accordance with this aspect of the invention, there is provided a card for the assay, which includes a plurality of separated marked areas for receiving serial dilutions of a gentamicin serum sample, and which further includes a plurality of separate marked areas for receiving gentamicin standard, whereby serial dilution of the sample can be conducted directly on the card, followed by conducting the assay and reading inhibition of agglutination directly on the card.

The preferred embodiment for conducting an inhibition of agglutination assay for gentamicin in accordance with the present invention will be further described with respect to the following example and the accompanying drawing wherein:

The drawing is an elevational view of a card employed in the assay of the present invention.

EXAMPLE 4

Reagents

1. Sensitized gentamicin particle suspension 1.0% of the sensitized particles prepared in Example 3, 0.05% polysorbate 80, 0.1 M glycine buffer, pH 8.2, 0.17 M sodium chloride, 0.2% sodium azide (preservative), and 0.5% ovalbumin.

2. Gentamicin Standards containing 0.6, 0.5, 0.4 and 0.3 micrograms ($\mu$g) gentamicin per milliliter (ml), 0.05 M phosphate buffered saline, pH 7.4, 0.1% sodium azide (preservative), and 10% human serum.

3. Gentamicin Antibody from Example 1 diluted in 50% human serum and 0.05 M phosphate buffered saline, pH 7.4, to obtain appropriate reactivity with gentamicin sensitized particles and gentamicin standards, 0.1% sodium azide (preservative).

4. Buffered Diluent contains 0.05 M phosphate buffered saline, pH 7.4 containing 0.1% sodium azide (preservative) and 20% human serum.

PROCEDURE

Place 25 microliters of buffered diluent onto the circles designated 2, 4, 8, 16, 32, 10, 20, 6, 12 and 24 of the card of the drawing followed by placing of 100 microliters onto circle 5 and 50 microliters onto circle 3.

25 Microliters of a serum sample is added to the buffered diluent in circle 2 and thoroughly mixed. 25 Microliters of the diluted sample of circle 2 is transferred to circle 4 and mixed. Employing the same procedure, the serial dilution is completed in the first horizontal row of the card; namely, circles 8, 16 and 32, with 25 microliters being drawn up and discarded from the last circle of the row. Each circle now contains a dilution of test sample, the reciprocal of which is the number found at the lower right of the circle.

25 Microliters of serum sample is dispensed onto circle 5 of the card and mixed. Serial dilution is then completed for the next two circles; namely circles 10 and 20, employing the hereinabove described procedure. 75 Microliters from circle 5 is then discarded, by discarding three 25 microliter aliquots.

25 Microliters of serum sample is dispensed onto circle 3. The sample is then serial diluted to the remaining horizontal circles in the row; namely circles 6, 12, 24, by the procedure hereinabove described. 25 Microliters is then discarded from circle 3.

As a result of the above procedure there are now 25 microliters of a 1:2, 1:4, 1:8, 1:16, 1:32, 1:5, 1:10, 1:20, 1:3, 1:6, 1:12 and 1:24 dilution of serum sample in circles 2, 4, 8, 16, 32, 5, 10, 20, 3, 6, 12 and 24, respectively.

25 Microliters of 0.6 microgram per ml. gentamicin standard is applied to the first standard circle (designated 0.6) on the card. The procedure is then repeated for the remaining standard circles marked 0.5, 0.4 and 0.3, employing the corresponding gentamicin standard.

25 Microliters of antibody is then dispensed onto all test and standard circles on the card, followed by mixing and spreading the reactants on each of the sample circles to thereby fill the entire circle. This is then followed by mixing and spreading of all standard circles.

The sensitized gentamicin particle suspension is then placed onto all test and standard circles in an amount of approximately 1/60 ml. The card is then rotated three or four times back and forth by hand, followed by placing the card on a mechanical rotator and rotation for 8 minutes under a moistened humidifier. Immediately subsequent to mechanical rotation, the card is then hand rotated using three or four back and forth motions. Under a high intensity lamp, the standard circles from 0.3 to 0.6 is read to determine the lowest concentration of standard which shows no clumping; i.e., inhibition of agglutination. This is followed by determination of the test circle with the highest dilution (lowest concentration) which shows no clumping; i.e., inhibition of agglutination.

The test results can be recorded directly on the card, and the concentration of gentamicin in the test sample can be calculated by multiplying the lowest standard concentration which shows no clumping (100% inhibition), by the highest reciprocal dilution of test specimen which shows no clumping (100% inhibition). For example, if the 0.5 microgram/ml standard shows no clumping and circle 16 shows no clumping, while circle 0.4 micrograms per ml and circle 20 shows clumping, then multiplying 0.5 times 16 gives a result of 8 micrograms per ml. gentamicin in the test specimen.

The standard circles marked 0.3 and 0.6 serve as reagent controls. The circle marked 0.3 is a reactive control and should show definite clumping. Circle 0.6 is a nonreactive control and should show no clumping.

The hereinabove described invention is particularly advantageous. In particular, the method is simple and enables the determination of gentamicin drug levels with less than 15% error. In addition, by employing two different carrier proteins for preparing gentamicin conjugates; namely, bovine serum albumin for the immunogen and orosomucoid for the sensitized particles, the need for cross adsorption of antisera is eliminated. In addition, antibodies to the orosomucoid carrier protein have not been found in over 300 human sera tested.

The gentamicin-protein conjugate supported on solid particles, which have been cross-linked, have been found to be stable for at least six months without any diminution in reactivity.

The use of the card test enables the dilution to be performed directly on the card. The twelve discontinuous drug levels that can be determined makes the test quantitative for drug levels. The test can detect as little as 1.0 microgram gentamicin per milliliter of serum. In the study of 56 clinical patient of volunteer sera, no major discrepancies were observed between card test results and radioimmunoassay results. The present test offers the further advantage that test results can be obtained in about a total of 11 minutes whereby patients on gentamicin can be tested at bedside to obtain adequate peak or trough data.

The use of gentamicin standards on the card test as internal controls minimizes the affect of variability of reading end points on card test results.

These and other advantages should be apparent to those skilled in the art from the teachings herein.

Numerous modifications and variations of the present invention are possible in light of the above teachings and, therefore, within the scope of the appended claims, the invention may be practised otherwise than as particularly described.

I claim:

1. A product comprising:
   a gentamicin-protein conjugate adsorbed on a solid support, said conjugate being crosslinked by a crosslinking agent to increase the stability thereof.

2. The product of claim 1 wherein the crosslinking agent is a dialdehyde.

3. An assay for gentamicin by agglutination wherein gentamicin-protein conjugate adsorbed on a solid particulate support is contacted with gentamicin antibody and sample, the improvement comprising:
   said conjugate on said solid particulate support being the product of claim 1.

4. The product of claim 1 wherein the solid support is polymer particles.

5. The product of claim 4 wherein the polymer is polystyrene.

6. The product of claim 1 wherein the crosslinking agent is glutaraldehyde.

7. The product of claim 6 wherein the support is polystyrene particles.

8. The product of claim 1 wherein the surface of the solid support also has a protein adsorbed thereon, said conjugate and said protein being formed into a crosslinked network by the crosslinking agent.

9. The product of claim 8 wherein the support is polymer particles.

10. The product of claim 8 wherein the crosslinking agent is a dialdehyde.

11. The product of claim 10 wherein the protein adsorbed on the surface of the solid support is ovalbumin, the crosslinking agent is glutaraldehyde and the support is polystyrene particles.

12. A product comprising:
    a conjugate of gentamicin and orosomucoid, said conjugate being supported on a solid support.

13. The product of claim 12 wherein the solid support is a particulate support.

14. In an agglutination assay for gentamicin wherein supported gentamicin is contacted with a sample and antibody to gentamicin, the improvement comprising:
    said supported gentamicin being the product of claim 13.

15. The product of claim 13 wherein the conjugate is crosslinked by a crosslinking agent to increase the stability thereof.

16. The product of claim 15 wherein the crosslinking agent is glutaraldehyde.

17. The product of claim 16 wherein the solid support is polystyrene particles, said solid support having a protein adsorbed thereon, said crosslinking agent forming the protein and conjugate into a crosslinked network.

18. In an assay for gentamicin by agglutination wherein gentamicin-protein conjugate adsorbed on a solid particulate support is contacted with gentamicin antibody and sample, the improvement comprising:
    said conjugate on said solid particulate support being the product of claim 16.

19. A kit for the assay of gentamicin by an agglutination procedure, comprising:
    a gentamicin-protein conjugate adsorbed on a solid particulate support, said conjugate being crosslinked by a crosslinking agent to increase the stability thereof; and
    antisera to gentamicin.

20. The kit of claim 19 wherein said anti-sera to gentamicin was produced by an immunogen comprised of gentamicin conjugated to a protein other than the protein of the gentamicin-protein conjugate adsorbed on the solid particulate support.

21. The kit of claim 20 wherein the protein of the supported gentamicin-protein conjugate is orosomucoid.

22. The kit of claim 21 wherein the protein of the immunogen is bovine serum albumin.

23. The kit of claim 19 and further comprising gentamicin standards.

24. The kit of claim 23 wherein the particulate support is a polymer.

25. The kit of claim 24 wherein the crosslinking agent is glutaraldehyde.

26. The kit of claim 25 wherein the surface of the solid support also has a protein adsorbed thereon, said conjugate and adsorbed protein being formed into a crosslinked network by the crosslinking agent.

27. The kit of claim 26 wherein the particles are polystyrene particles.

28. The kit of claim 27 wherein the protein of the conjugate is orosomucoid.

29. An improved card assay kit for determination of gentamicin by an agglutination procedure, comprising:
a gentamicin-protein conjugate comprised of orosomucoid as the protein supported on a solid particulate support;
an antibody to gentamicin; and
an assay card, said assay card including a plurality of separated marked areas for receiving serial dilutions of a gentamicin sample and a plurality of separated marked areas for receiving gentamicin standard, whereby serial dilution of a sample and assay thereof can be conducted on the card.

30. The kit of claim 29 and further comprising gentamicin standard.

31. The kit of claim 30 wherein the conjugate is adsorbed on the solid support, said conjugate being crosslinked by a crosslinking agent to increase the stability thereof.

32. The kit of claim 31 wherein the crosslinking agent is glutaraldehyde.

33. The kit of claim 32 wherein the particulate support is polystyrene.

34. The kit of claim 33 wherein the particulate support has a protein adsorbed on the surface thereof, said conjugate and adsorbed protein being formed in a crosslinked network by the crosslinking agent.

35. An improved card assay kit for determination of gentamicin by an agglutination procedure, comprising:
a gentamicin-protein conjugate supported on a solid particulate support;
an antibody to gentamicin;
gentamicin standard; and
an assay card, said assay card having a surface including a sample portion and a standard portion, said sample portion being comprised of at least one series of separated marked serial dilution areas for receiving at least one series of serial dilutions of a gentamicin sample, each of which has an indicia of the dilution, said standard portion including at least two separated marked standard areas for receiving gentamicin standard of different gentamicin concentration, each having an indicia of the gentamicin concentration, whereby a quantitative determination of gentamicin in a sample can be determined directly on the card by serial dilution of sample on the card, adding antibody to gentamicin and the gentamicin-protein conjugate to the serial diluted gentamicin samples and gentamicin standards and determining the lowest standard concentration and the highest dilution at which agglutination is inhibited.

* * * * *